United States Patent [19]
Ohno et al.

[11] Patent Number: 5,250,416
[45] Date of Patent: Oct. 5, 1993

[54] METHOD FOR HIGHLY SENSITIVE DETERMINATION OF NADH USING KINASE

[75] Inventors: Tsuyoshi Ohno, Matsudo; Masaru Suzuki; Tatsuo Horiuchi, both of Nagareyama; Yasushi Shirahase; Koji Kishi, both of Kobe; Yoshifumi Watazu, Akashi, all of Japan

[73] Assignees: Noda Institute for Scientific Rsearch, Chiba; International Reagents Corp., Hyogo, both of Japan

[21] Appl. No.: 823,113

[22] Filed: Jan. 21, 1992

[30] Foreign Application Priority Data

Jan. 25, 1991 [JP] Japan .................. 3-007999

[51] Int. Cl.$^5$ .................. C12Q 1/48; C12Q 1/26; C12P 19/36; C12N 9/96
[52] U.S. Cl. .................. 435/15; 435/25; 435/90; 435/188
[58] Field of Search .............. 435/15, 25, 188, 90

[56] References Cited

U.S. PATENT DOCUMENTS

| | | | |
|---|---|---|---|
| 4,411,995 | 10/1983 | Whitesides et al. | 435/90 |
| 4,416,983 | 11/1983 | Röder | 435/25 |
| 4,446,231 | 5/1984 | Self | 435/7 |
| 4,501,813 | 2/1985 | Lövgren | 435/8 |
| 4,598,042 | 7/1986 | Self | 435/7 |
| 4,766,071 | 8/1988 | Simon | 435/90 |
| 4,769,321 | 9/1989 | Self | 435/7 |
| 5,032,506 | 7/1991 | Palmer | 435/26 |

FOREIGN PATENT DOCUMENTS 58-129994 3/1983 Japan.
59-213400 3/1984 Japan.

OTHER PUBLICATIONS

Iwahashi, et al., "Localization of the NADH Kinase in the Inner Membrane of Yeast Mitochondria", J. Biochem., 105:916–921 (1989).
Iwahashi, et al., "Characterization of NADH Kinase from *Saccharomyces cerevisiae*", J. Biochem. 105:588–693 (1989).
Iwahashi, et al., "Orientation and Reactivity of NADH Kinase in Proteoliposomes", J. Biochem., 105:922–926 (1989).
World Patents Index Latest Weeek 9232, Derwent Publications Ltd., London, BG; AN92-260430 & DE-A-4 201 930 (Noda Inst Sci Res) Jul. 30, 1992, Abstract

*Primary Examiner*—Michael G. Wityshyn
*Assistant Examiner*—Ralph G. Gitomer
*Attorney, Agent, or Firm*—Banner, Birch, McKie & Beckett

[57] ABSTRACT

The present invention relates to a method for determining a slight amount of NADH or XTP which is present in a solution, with high sensitivity by the use of an NADH kinase specific for NADH by utilizing a cycling reaction, and this method permits highly sensitive determination of NADH without any influence of NAD+ and hence is useful for diagnoses of diseases and the like.

2 Claims, 13 Drawing Sheets

LEVEL OF 3-HYDROXY BUTYRIC DEHYDROGENASE ACTIVITY (IU/L)

METHOD FOR HIGHLY SENSITIVE DETERMINATION OF NADH USING KINASE

BACKGROUND OF THE INVENTION

The present invention permits accurate diagnoses mainly of diseases and the like by highly sensitive determination of a substance capable of serving as a marker of pathosis, by the use of an NADH kinase highly specific for NADH, and can be utilized in the fields of clinical diagnoses, therapeutics, etc.

DESCRIPTION OF THE PRIOR ART

Now, there is widely employed a diagnostic method in which the amount of a substance capable of serving as a marker of pathosis is determined using an enzymatic reaction. However, there exist trace markers which are difficult to measure by conventional methods, and the amount of a test fluid is limited to a slight amount in some cases, for example, medical examinations of newborn babies. Highly sensitive analytical methods capable of solving such problems are desirable.

One of such methods is a sensitizing analytical method using a cycling reaction. As the cycling reaction, there are known $\beta$-NAD+$\leftrightarrow$$\beta$-NADH cycling reaction, $\beta$-NADP+$\leftrightarrow$$\beta$-NADPH cycling reaction, etc. ["Seikagaku Jikken Koza (Biochemical Experiments)", Vol. 5, p. 121-131]. For example, as disclosed in Japanese Patent Unexamined Publication No. 59-213400, $\beta$-NAD+ can be determined with high sensitivity by phosphorylating only $\beta$-NAD+ in a solution containing $\beta$-NADH and $\beta$-NAD+, into $\beta$-NADP+ by the use of a kinase specific for $\beta$-NAD+, and subjecting the $\beta$-NADP+ to the cycling reaction.

However, when a slight amount of NADH is present in a mixture comprising NAD+ (hereinafter referring to $\beta$-NAD+, thio-NAD+ or $\alpha$-NAD+) and NADH ($\beta$-NADH, thio-NADH or $\beta$-NADH), it cannot be determined by the above method disclosed in Japanese Patent Unexamined Publication No. 59-213400. Therefore, there have heretofore been employed a flow injection assay using HPLC and a method comprising boiling (Japanese Patent Unexamined Publication No. 58-129994), but there methods are disadvantageous in that they require an expensive apparatus, a troublesome procedure and a long time. There are also a highly sensitive method comprising allowing $\beta$-NADH to cause luminescence by the use of luciferase and a method comprising allowing $\beta$-NADH to cause chemiluminescence, but these methods require a special and expensive detector and involve the problem of the stability of reagents.

SUMMARY OF THE INVENTION

In consideration of such conditions, the present inventors earnestly investigated a method for determining a slight amount of NADH with high sensitivity in the case where excess NAD+ is present. Consequently, it was found that this purpose can be achieved by the use of a kinase which acts specifically on NADH. As a result of further investigation, the present inventors found that also in a mixture comprising NAD+ and a slight amount of NADH, NADH can be determined with high sensitivity by phosphorylating only NADH into NADPH and subjecting the NADPH to the cycling reaction, and that highly sensitive determination of a slight amount of XTP can also be made possible, whereby the present invention was accomplished.

The present invention provides a method for highly sensitive determination of NADH which comprises allowing an NADH kinase highly specific for NADH (hereinafter referred to as the present enzyme) to act on a solution containing NAD+ and NADH, in the presence of divalent metal ions and XTP [wherein X is A (adenosine), U (uridine), G (guanosine), C (cytidine), I (inosine), dT (thymidine), dA (deoxyadenosine), dU (deoxyuridine), dG (deoxyguanosine), dC (deoxycytidine), or dI (deoxyinosine)], to produce XDP (wherein X is as defined above) and NADPH; subjecting the NADPH to the cycling reaction by using a catalytic reaction capable of oxidizing NADPH into NADP+ and a catalytic reaction capable of reducing NADP+ into NADPH; measuring the variable amount of a substrate consumed by the cycling reaction or a product produced by the cycling reaction; and thereby determining the amount of only NADH in the mixed solution containing NAD+ and NADH.

The present invention further provides a method for highly sensitive determination of XTP which comprises allowing an NADH kinase highly specific for NADH to act on a solution containing XTP [wherein X is A (adenosine), U (uridine), G (guanosine), C (cytidine), I (inosine), dT (thymidine), dA (deoxyadenosine), dU (deoxyuridine), dG (deoxyguanosine), dC (deoxycytidine), or dI (deoxyinosine)] in the presence of divalent metal ions and NADH to produce XDP (wherein X is as defined above) and NADPH; subjecting the NADPH to the cycling reaction by using a catalytic reaction capable of oxidizing NADPH into NADP+ and a catalytic reaction capable of reducing NADP into NADPH; measuring the variable amount of a substrate consumed by the cycling reaction or a product produced by the cycling reaction; and thereby determining the amount of XTP.

The above NAD+ includes $\beta$-NAD+, thio-NAD+ and $\alpha$-NAD+. The above NADH includes $\beta$-NADH, thio-NADH and $\alpha$-NADH.

The above divalent metal ion includes $Mg^{2+}$, $Mn^{2+}$, $Ca^{2+}$, $Co^{2+}$, etc. A catalyst for the oxidation includes dehydrogenases, diaphorases, NAD(P)H oxidase and electron carriers. The electron carriers include Meldola's Blue (9-dimethylamino-benzo-$\alpha$-phenazoxonium chloride), 1-methoxy PMS (1-methoxy-5-methylphenazinium methylsulfate), PMS (methylphenazinium methylsulfate), PQQ (pyrroloquinoline quinone), etc. A catalyst for the reduction includes dehydrogenases, and NADP+-dependent dehydrogenases are particularly preferable.

DESCRIPTION OF THE PREFERRED EMBODIMENTS

Figure 1:
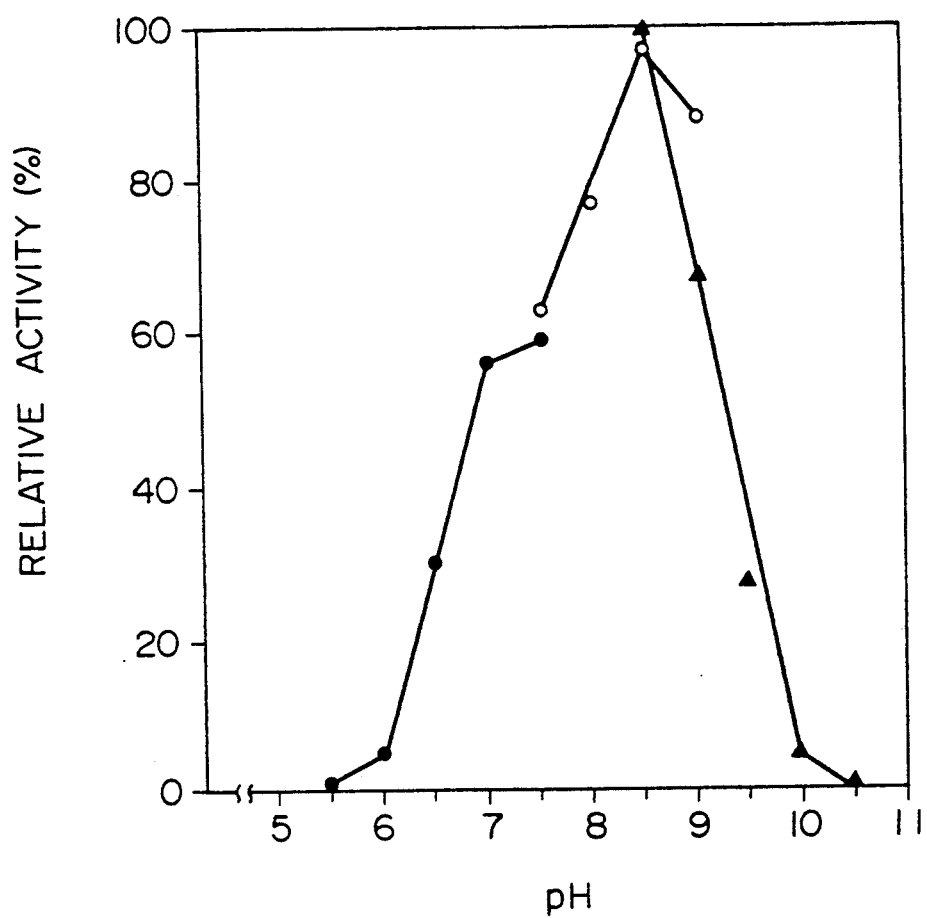
FIG. 1 is a graph showing the optimum pH of the present enzyme (●-●: phosphate buffer, O-O: Tris-HCl buffer, ▲-▲: glycine-sodium hydroxide buffer).

The present invention is explained below in detail.

First, an outline of reactions in the highly sensitive determination of the present invention is shown below.

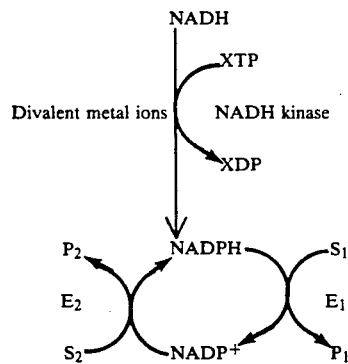

wherein the symbols have the following meanings:

$E_1$: an oxidation catalyst capable of catalyzing a reaction by which NADP+ and $P_1$ may be produced from substrates NADPH and $S_1$.

$E_2$: a reduction catalyst capable of catalyzing a reaction by which NADPH and $P_2$ may be produced from substrates NADP+ and $S_2$.

$S_1$: an oxidized-form substrate for $E_1$.

$S_2$: a reduced-form substrate for $E_2$.

$P_1$: a reduced-form product produced from $S_1$ by $E_1$.

$P_2$: an oxidized-form product produced from $S_2$ by $E_2$.

XTP: X = A: adenosine-5'-triphosphate
= U: uridine-5'-triphosphate
= G: guanosine-5'-triphosphate
= C: cytidine-5'-triphosphate
= I: inosine-5'-triphosphate -continued = dT: thymidine-5'-triphosphate
= dA: 2'-deoxyadenosine-5'-triphosphate
= dU: 2'-deoxyuridine-5'-triphosphate
= dG: 2'-deoxyguanosine-5'-triphosphate
= dC: 2'-deoxycytidine-5'-triphosphate
= dI: 2'-deoxyinosine-5'-triphosphate XDP: each of the same compounds as above except that triphosphate is replaced by diphosphate.

A solution to be tested by the method of the present invention may be any solution so long as it contains NAD+ and NADH as a mixture. As such a solution, there can be exemplified solutions containing both NAD+ and NADH, and solutions containing NADH liberated and produced by any of various enzymatic reactions. Specific examples of the solution are reaction solutions containing NADH produced from NAD+ consumed as substrate by enzymatic reaction by dehydrogenase, for example, the reaction solutions 1 to 20 shown below. These reactions systems exemplified, however, are not intended in any way to limit the solution to be tested by the method of the present invention. The solution to be tested by the method of the present invention may be any solution so long as it contains XTP. As such a solution, there can be exemplified reaction solutions containing XTP produced from XDP consumed by enzymatic reaction by kinase, for example, the reaction solutions 21 to 29 shown below. These reactions systems exemplified, however, are not intended in any way to limit the solution to be tested by the method of the present invention.

In the following formulas, the symbol "DH" is used as an abbreviation of dehydrogenase.

1. 3α-Hydroxysteroid + NAD+ $\xrightarrow{\text{3α-Hydroxysteroid DH}}_{\text{[EC 1.1.1.50]}}$ 3-Oxosteroid + NADH + H+

2. R—CH$_2$OH + NAD+ $\xrightarrow{\text{Alcohol DH}}_{\text{[EC 1.1.1.1]}}$

R—CHO + NADH + H+

(wherein R is an alkyl group or the like)

3. Glycerin + NAD+ $\xrightarrow{\text{Glycerol DH}}_{\text{[EC 1.1.1.6]}}$

Dihydroxyacetone + NADH + H+

4. sn-Glycerol-3-phosphate + NAD+ $\xrightarrow{\text{Glycerol-3-phosphate DH}}_{\text{[EC 1.1.1.8]}}$ Dihydroxyacetone phosphate + NADH + H+

5. L-lactate + NAD+ $\xrightarrow{\text{Lactate DH}}_{\text{[EC 1.1.1.27]}}$

Pyruvic acid + NADH + H+

6. L-malate + NAD+ $\xrightarrow{\text{Malate DH}}_{\text{[EC 1.1.1.37]}}$

Oxaloacetic acid + NADH

7. L-carnitine + NAD+ $\xrightarrow{\text{Carnitine DH}}_{\text{[EC 1.1.1.108]}}$ 3-Dehydrocarnitine + NADH + H+

-continued

8. Formate + NAD+ $\xrightarrow{\text{Formate DH} \atop [\text{EC 1.2.1.2}]}$ CO$_2$ + NADH 9. Formaldehyde + Glutathione + NAD+ $\xrightarrow{\text{Formaldehyde DH} \atop [\text{EC 1.2.1.1}]}$ S-Formylglutathione + NADH + H$^+$ 10. Isocitrate + NAD+ $\xrightarrow{\text{Isocitrate DH} \atop [\text{EC 1.1.1.41}]}$ 2-Oxoglutarate + CO$_2$ + NADH 11. D-lactate + NAD+ $\xrightarrow{\text{D-Lactate DH} \atop [\text{EC 1.1.1.28}]}$ Pyruvic acid + NADH + H$^+$ 12. R—CHO + H$_2$O + NAD+ $\xrightarrow{\text{Aldehyde DH} \atop [\text{EC 1.2.1.3}]}$

R—COO$^-$ + NADH + 2H$^+$

13. Xanthine + H$_2$O + NAD+ $\xrightarrow{\text{Xanthine DH} \atop [\text{EC 1.2.1.37}]}$ Uric acid + NADH + H$^+$ 14. L-fucopyranose + NAD+ $\xrightarrow{\text{L-Fucose DH} \atop [\text{EC 1.1.1.122}]}$ L-fucono-1,5-lactone + NADH + H$^+$ 15. D-3-hydroxybutyric acid + NAD+ $\xrightarrow{\text{3-Hydroxybutyrate DH} \atop [\text{EC 1.1.1.30}]}$ 3-Oxobutyrate + NADH + H$^+$ 16. D-galatofuranose + NAD+ $\xrightarrow{\text{Galactose DH} \atop [\text{EC 1.1.1.48}]}$ D-galactono-γ-lactone + NADH + H$^+$ 17. Testosterone + NAD+ $\xrightarrow{\text{Testosterone-17}\beta\text{-DH} \atop [\text{EC 1.1.1.63}]}$ 4-Androstene-3,17-dione + NADH + H$^+$ 18. L-alanine + H$_2$O + NAD+ $\xrightarrow{\text{Alanine DH} \atop [\text{EC 1.4.1.1}]}$ Pyruvic acid + NH$_4^+$ + NADH + H$^+$ 19. L-glutamate + H$_2$O + NAD+ $\xrightarrow{\text{Glutamate DH} \atop [\text{EC 1.4.1.2}]}$ 2-Oxoglutarate + NH$_4^+$ + NADH + H$^+$ 20. 3α,7α,12α-Trihydroxy-5β-cholanate +

NAD+ $\xrightarrow{\text{7α-Hydroxysteroid DH} \atop [\text{EC 1.1.1.159}]}$

3α,12α-Dihydroxy-7-oxo-5β-cholanate + NADH + H$^+$

21. Creatine phosphate + ADP $\xrightarrow{\text{Creatine kinase} \atop [\text{EC 2.7.3.2}]}$ Creatine + ATP (in the presence of Mg$^{2+}$)

22. Phosphoenolpyruvic acid + ADP $\xrightarrow{\text{Pyruvate kinase} \atop [\text{EC 2.7.1.40}]}$ Pyruvic acid + ATP (in the presence of Mg$^{2+}$ or Mn$^{2+}$, and K$^+$ or NH$_4^+$)

23. Acetylphosphoric acid + ADP $\xrightarrow{\text{Acetate kinase} \atop [\text{EC 2.7.2.1}]}$ -continued Acetic acid + ATP 24. Carbamoylphosphoric acid + ADP $\xrightarrow{\text{Carbamate kinase} \atop [\text{EC 2.7.2.2}]}$

NH$_3$ + CO$_2$ + ATP (in the presence of Mg$^{2+}$, Mn$^{2+}$ or Co$^{2+}$)

25. L-aspartate 4-phosphate + ADP $\xrightarrow{\text{Aspartate kinase} \atop [\text{EC 2.7.2.4}]}$ L-aspartate + ATP (in the presence of Mg$^{2+}$ or Mn$^{2+}$)

26. D-1,3-bisphosphoglycerate + ADP $\xrightarrow{\text{Phosphoglycerate kinase} \atop [\text{EC 2.7.2.3}]}$ 3-Phospho-D-glycerate + ATP (in the presence of Mg$^{2+}$ or Mn$^{2+}$)

27. Arginine phosphate + ADP $\xrightarrow{\text{Arginine kinase} \atop [\text{EC 2.7.3.3}]}$ L-arginine + ATP (in the presence of Mg$^{2+}$ or Mn$^{2+}$)

28. ADP + ADP $\xrightarrow{\text{Adenylate kinase} \atop [\text{EC 2.7.4.3}]}$

AMP + ATP (in the presence of Mg$^{2+}$, Mn$^{2+}$, Ca$^{2+}$, etc.)

29. XDP + ADP $\xrightarrow{\text{Nucleosidemonophosphate kinase} \atop [\text{EC 2.7.4.4}]}$ XMP + ATP (in the presence of Mg$^{2+}$, Mn$^{2+}$, Co$^{2+}$ or Ca$^{2+}$)

(wherein X is U, I, G, C, A, dT, dU, dG, dC or dA)

The solutions 1 to 20 are examples of solutions for determining NADH produced by enzymatic reaction by each dehydrogenase. In the case of these solutions, one of factors in such enzymatic reaction systems, i.e., the enzymatic activity of dehydrogenase, the amount of NAD+ and the amount of a substrate for the enzyme which is consumed together within NAD+, can be determined by determining the amount of NADH. The solutions 21 to 29 are examples of solutions for determining ATP produced by enzymatic reaction by each kinase. In the case of these solutions, one of factors in such enzymatic reaction systems, i.e., the enzymatic activity of kinase, the amount of ADP and the amount of a phosphorus-containing compound as substrate for the enzyme which is consumed together with ADP, can be determined by determining the amount of ATP.

The above substances to be quantitatively determined may be those produced by another series of reaction systems. In this case, one of factors participating in a reaction carried out at the very first can be quantitatively determined after all.

The above various enzymatic reactions can be carried out simultaneously with enzymatic reaction by NADH kinase.

An outline of the over-all reaction in this case is shown below.

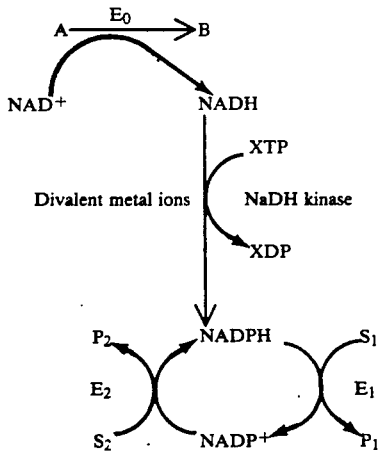

wherein the symbols have the following meanings:

$E_0$: a dehydrogenase capable of catalyzing a reaction by which NADH and B are produced from substrates NAD+ and A.

A: a reduced-form substrate for dehydrogenase $E_0$.

B: an oxidized-form product produced from A by dehydrogenase $E_0$.

$E_1$, $E_2$, $S_1$, $S_2$, $P_1$ and $P_2$: the same as defined above.

In the above enzymatic reaction systems, conditions (e.g. temperature, pH, and necessity for a stabilizer and metal ions) for carrying out the reactions are properly determined in accordance with conventional techniques. The reaction temperature may be usually 20° to 40° C. The pH at reaction is properly adjusted to 6.0 to 9.5 depending on an enzymatic reaction to be carried out, by choosing and using a suitable buffer solution having a pH in this pH range. As the buffer solution, there can be used, for example, phosphate buffers and various Good's buffers. The reaction time is a time required for each enzymatic reaction and is not critical.

As the NADH kinase used in the present invention, any kinase may be used so long as it acts specifically on NADH and has a stability sufficient for practical purposes. There can be exemplified NADH kinase having the following physicochemical properties (hereinafter referred to as "the present enzyme").

(1) Action

The present enzyme, as shown in the reaction formula given below, catalyzes a reaction by which NADPH and XDP (wherein X is as defined above) are produced from substrates NADH and XTP (wherein X is as defined above) through phosphorylation of NADH in the presence of at least one kind of ions selected from the group consisting of $Mg^{2+}$, $Mn^{2+}$, $Ca^{2+}$ and $Co^{2+}$ ions.

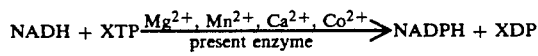

wherein X is as defined above.

(2) Substrate Specificity

The present enzyme has a very high specificity for NADH and hardly acts on NAD+.

The substrate specificity of the present enzyme was examined under the following reaction conditions.

TABLE 1

| Substrate solution | |
|---|---|
| 10 mM NADH or NAD+ | 0.2 ml |
| 0.5 mM HEPPS* buffer (pH 8.5) | 0.1 ml |
| 10 mM ATP | 0.3 ml |
| 0.1 M magnesium chloride | 0.1 ml |
| 2.0 M sodium acetate | 0.1 ml |
| | 0.9 ml |

*HEPPS: N-2-Hydroxyethylpiperazine-N'-3-propanesulfonic acid

To 0.9 ml of each of the substrate solutions containing NADH or NAD+, respectively, shown in Table 1 was added 0.1 ml of 23 U/ml of the present enzyme, and the reaction was carried out at 30° C. for 20 minutes. Then, the reaction was terminated by heat treatment at 100° C. for 2 minutes, and the denatured protein was removed, after which the amount of NADPH or NADP+ produced by the reaction of the corresponding substrate was measured as follows. As a control solution, there was used a mixture of each substrate solution and the present enzyme in which the reaction had been terminated immediately after mixing them.

With 1 ml of each of the reaction solutions obtained in the above was mixed 1 ml of a color-producing solution consisting of 10 mM G-6-P, 50 mM HEPPS buffer (pH 8.0), 10 mM magnesium chloride, 0.1% bovine serum albumin, 2.5 IU/ml G-6-P dehydrogenase (NADP+-dependent), 5 IU/ml diaphorase and 250 μM 2,6-dichlorophenolindophenol. The resulting mixture was immediately introduced into a constant-temperature cuvette of STASAR III spectrophotometer of Gilford and subjected to reaction at 30° C. Simultaneously with the reaction, the change of absorbance at 600 nm was measured with the lapse of time, and the difference ($\Delta OD_{600nm}$/min) between absorbance values 1 minute and 2 minutes after the initiation of the coloration reaction was taken as a measured value. As to the relative activity (%), a measured value ($\Delta OD_{600nm}$/min) obtained by using NAD+ as substrate was shown as a percentage based on a measured value ($\Delta OD_{600nm}$/min) obtained by using NADH as substrate.

The results obtained are as follows:

TABLE 2

| Substrate | Relative activity (%) |
|---|---|
| NADH | 100 |
| NAD+ | 0.9 |

| (3) Measuring method of titer | |
|---|---|
| Substrate solution | |
| 10 mM NADH | 0.2 ml |
| 0.5 M HEPPS buffer (pH 8.5) | 0.1 ml |
| 10 mM ATP | 0.3 ml |
| 0.1 M magnesium chloride | 0.1 ml |
| 2.0 M sodium acetate | 0.1 ml |
| Distilled water | 0.1 ml |
| | 0.9 ml |

0.9 Milliliters of the substrate solution containing NADH shown in Table 2 was preheated to 30° C., after which 0.1 ml of a solution of the present enzyme having an adequate concentration was added, and the reaction was carried out at 30°·C. for 20 minutes. Thereafter, the reaction was terminated by heat treatment at 100° C. for 2 minutes, and the denatured protein was removed. Then, the amount of NADPH produced by the reaction of the substrate was measured as follows. As a control solution, there was used a mixture of the substrate solution and the present enzyme in which the reaction had been terminated immediately after mixing them.

With 1 ml of each of the reaction solutions obtained in the above was mixed 1 ml of a color-producing solution having the same composition as that of the color-producing solution described in the above item "Substrate specificity". The resulting mixture was immediately introduced into a constant-temperature cuvette of STASAR III spectrophotometer of Gilford and subjected to reaction at 30° C. Simultaneously with the reaction, the change of absorbance at 600 nm was measured with the lapse of time, and the difference ($\Delta OD_{600nm}$/min) between absorbance values 1 minute and 2 minutes after the initiation of the coloration reaction was obtained as a measured value. By the use of a calibration curve of $\Delta OD_{600nm}$/min versus NADPH concentration previously prepared using NADPH solutions of known concentrations, the amount of the NADPH produced was calculated from the measured value.

An amount of the enzyme at which NADPH is produced in an amount of 1 nano-mole per minute at 30° C., is taken as 1 unit.

The Km value (Michaelis constant) of the present enzyme for NADH is 27 micromoles at 30° C. and pH 7.8 (Tris buffer).

(4) Optimum pH

The optimum pH of the present enzyme is, as shown in FIG. 1, pH 8.0-9.0 when NADH is used as a substrate.

(5) pH Range for Stability

Figure 2:
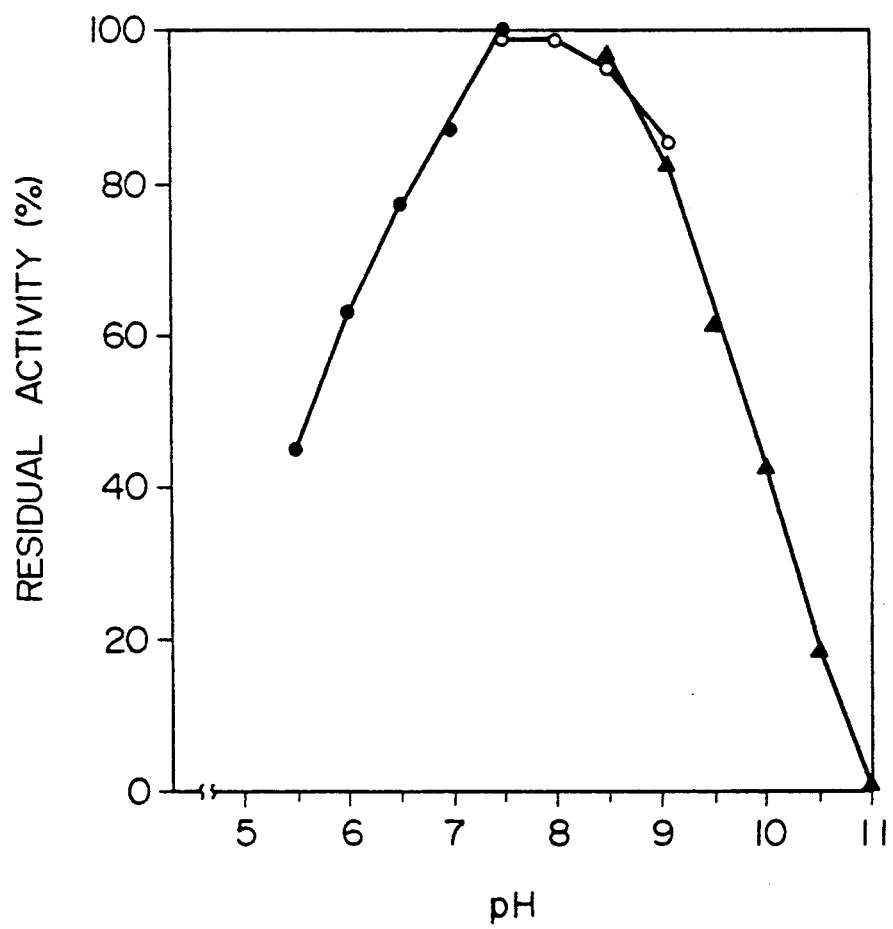
FIG. 2 is a graph showing a pH range for stability of the present enzyme (●-●: phosphate buffer, O-O: Tris-HCl buffer, ▲-▲: glycine-sodium hydroxide buffer).

The present enzyme was dissolved in each of buffer solutions of various pH, and after standing at 4° C. for 16 hours, the residual activity was measured to find that the enzyme was stable at pH 7.0-9.0 as shown in FIG. 2.

(6) Range of Temperature Suitable for Action

Figure 3:
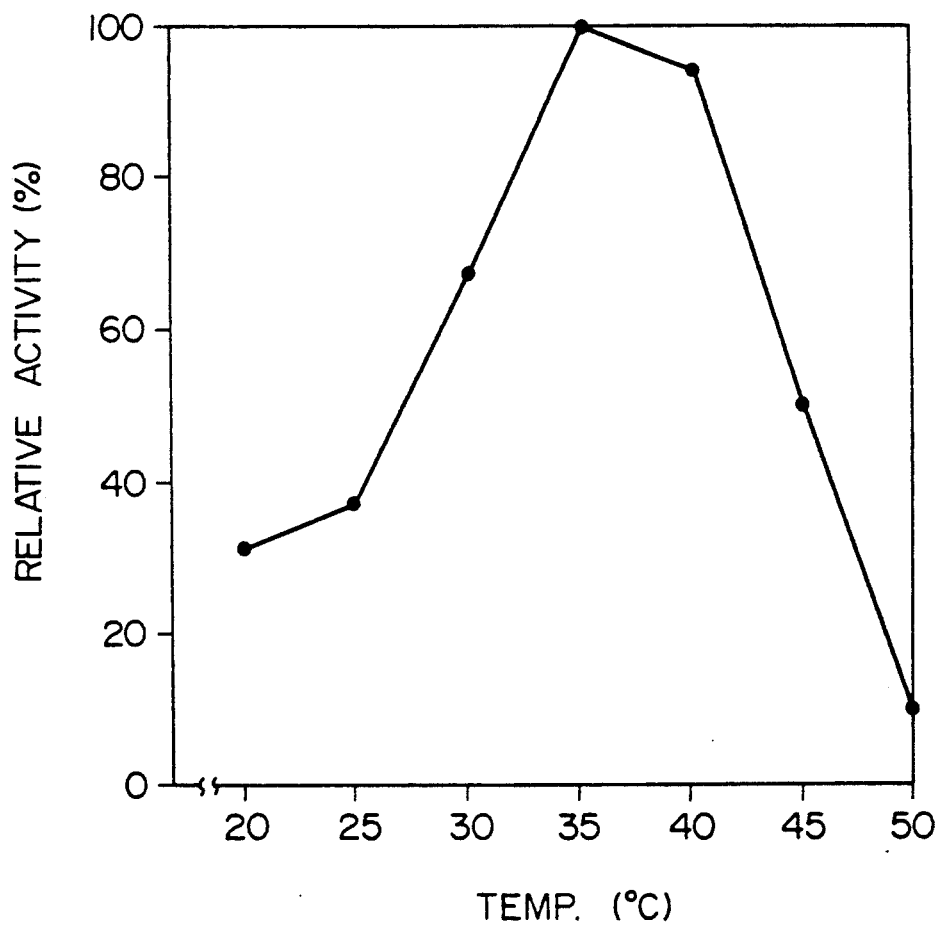
FIG. 3 is a graph showing a range of temperature suitable for action of the present enzyme.

The range of temperature suitable for action of the present enzyme is 30° to 45° C. as shown in FIG. 3.

(7) Thermal Stability

Figure 4:
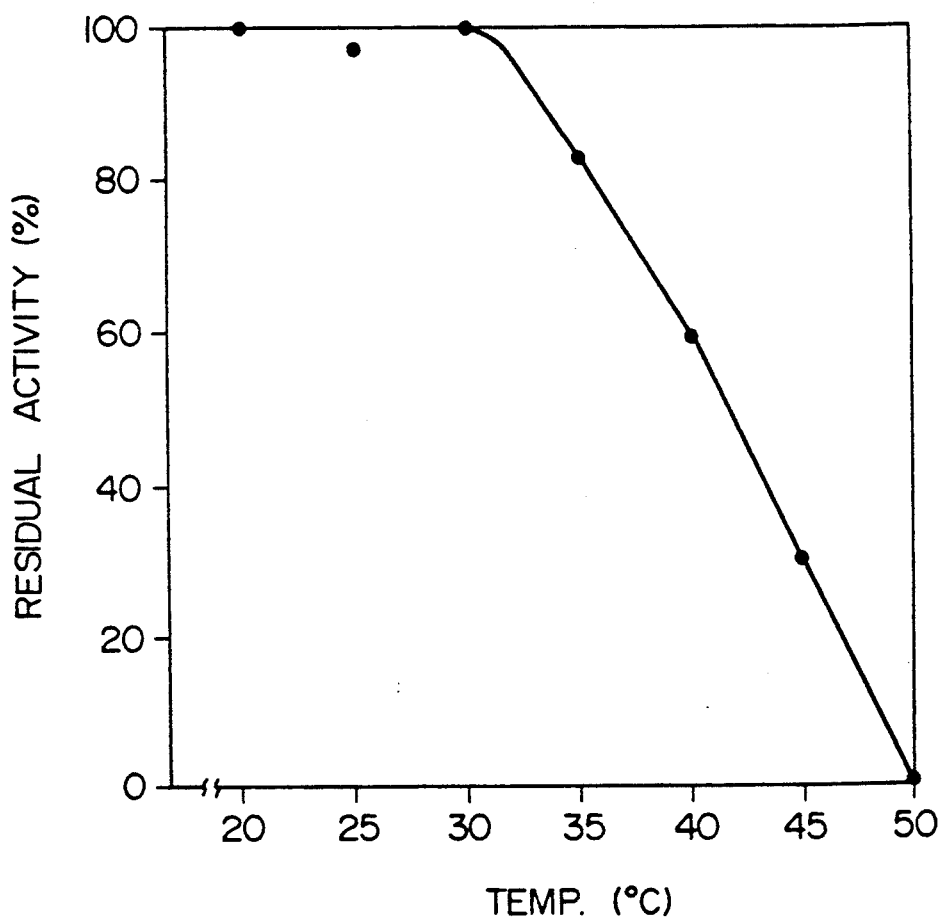
FIG. 4 is a graph showing the thermal stability of the present enzyme.

The present enzyme was dissolved in a buffer solution, and after standing at each temperature for 10 minutes, the residual enzymatic activity was measured, whereby the thermal stability was measured. Consequently, the present enzyme showed residual activity percentages of 83% at 35° C., 60% at 40° C., and 30% at 45° C. as shown in FIG. 4.

(8) Inhibition, Activation and Stabilization

The present enzyme is strongly inhibited by SDS (sodium lauryl sulfate), p-CMB (p-chloromercuribenzoic $Pb^{2+}$, $Zn^{2+}$, $Cd^{2+}$, $Cu^{2+}$, $Hg^{2+}$, etc., and is activated by sodium acetate, etc. In addition, it is stabilized by saccharose, $Mg^{2+}$, $Mn^{2+}$, dithiothreitol, N-acetyl-L-cysteine, ammonium sulfate, etc.

(9) Purification Method

The present enzyme can be purified by employing conventional methods for purification of enzymes, such as ion-exchange chromatography, ammonium sulfate fractionation, hydrophobic chromatography, gel filtration, etc. singly or in combination of two or more thereof.

(10) Molecular Weight

The molecular weight of the present enzyme is about 160,000 as measured by gel filtration using Superose 6 HR10/30 column [mfd. by Pharmacia AB (Sweden)] according to the method of Andrews [Biochem J. 96, 595 (1965)].

(11) Isoelectric Point

The isoelectric point of the present enzyme is pI=6.40 as measured by electrophoresis by the use of an agarose gel containing an ampholyte.

Comparison between the present enzyme and NADH kinases described in well-known references, i.e., NADH kinase A (J. Biochem. 105, 588-593, 1989) and NADH kinase B (J. Biochem. 247, 1473-1478, 1972), is as shown in Table 3.

TABLE 3

| | Present enyme | A | B |
|---|---|---|---|
| Source | Pichia membranae-faciens | Saccharomyces cerevisiae | Saccharomyces cerevisiae |
| Optimum pH | 8.5 | 8.5 | 8.0-8.5 |
| Thermal stability | 10% inactivated at 35° C. in 5 min. 17% inactivated at 35° C. in 10 min. | 65% inactivated at 35° C. in 5 min. | Very unstable |
| Specificity | NADH = 100 $NAD^+$ = 0.9 | NADH = 100 $NAD^+$ = 1.7 | NADH = 100 $NAD^+$ = 1.6 |
| Molecular weight | 160,000 | 160,000 | |

As is clear from Table 3, the present enzyme is different from the known NADH kinases in enzymological and physicochemical properties and is superior to them particularly in thermal stability. Therefore, the present enzyme can be used for practical purposes, for example, highly sensitive analysis using the present enzyme in combination with other various enzymes, and hence is very advantageous.

The present enzyme may be produced by culturing Pichia membranaefaciens YS27 (FERM BP-3208) in a nutrient broth. The present enzyme may be reacted usually at a pH of approximately 6.5-9.5 and usually at approximately 20°-40° C. Although the amount of the enzyme used is not critical, it is usually approximately 1-500 units.

As the divalent metal ion required for the reaction with NADH kinase, such as magnesium ion, manganese ion, calcium ion or cobalt ion, there may be used water-soluble salts capable of releasing these metal ions, for example, magnesium chloride, manganese chloride and calcium chloride. In the reaction system, the water-soluble salts may be used usually in a concentration of approximately 0.1-100 mM, preferably 1-20 mM.

As to the amount of ATP used for determining NADH, excess ATP over NADH in the solution may be used. Usually, ATP is used preferably in a concentration of approximately 0.1-10 mM in the reaction system.

An excess amount of NADH over ATP in the solution may be used for determining the ATP, but NADH is preferably used in a concentration of about 0.05 to 5 mM in the reaction system.

When reaction with any of various enzymes for $E_0$ and enzymatic reaction with NADH kinase are carried out at the same time, or when a series of many enzymatic reactions are carried out at the same time, the reactions are carried out by properly choosing a temperature and a pH at which the over-all reaction can be smoothly carried out, and satisfying conditions concerning various additives and the like.

As the above-mentioned catalyst $E_1$ for oxidation of NADPH which is used in the present invention, any enzyme may be used so long as it acts on NADPH produced together with ADP by the enzymatic reaction of ATP and NADH with NADH kinase, to catalyze a reaction by which a reduced-from product $P_1$ and $NADP^+$ are produced from the NADPH and an oxidized-form substrate $S_1$.

As catalyst $E_2$ for reduction of $NADP^+$ which is used for constitution of the cycling reaction in combination with catalyst $E_1$, any enzyme may be used so long as it acts on $NADP^+$ produced by $E_1$ as described above, to catalyze a reaction by which an oxidized-form product $P_2$ and NADPH are produced from the $NADP^+$ and a reduced-form substrate $S_2$.

When the enzymatic reactions by $E_1$ and $E_2$, respectively, are carried out in combination, NADPH produced by NADH kinase is converted into $NADP^+$ by $E_1$, and the $NADP^+$ is converted into NADPH by $E_2$, after which this NADPH is returned to the reaction by $E_1$. By this mechanism, the cycling reaction is constituted.

When at least either $E_1$ or $E_2$ is dependent on $NADP^+$, no cycling reaction is constituted for NAD(H), and hence only NADPH can be determined with high sensitivity.

In every cycle of the cycling reaction, the reaction by $E_1$ results in consumption of $S_1$ in an amount equimolar with the amount of NADPH and production of equimolar amounts of $P_1$ and $NADP^+$, and the reaction by $E_2$ results in consumption of $S_2$ in an amount equimolar with the amount of $NADP^+$ and production of equimolar amounts of $P_2$ and NADPH. For a certain amount of NADPH in the solution, the rate of the cycling reaction is rapider than that of the reaction by $E_1$ alone. Therefore, each substrate is needed in an amount of a number of moles larger than the number of cycles, per mole of a component to be quantitatively determined. Usually, each substrate is used in large excess. For example, it can be used in an amount of 10 to 10,000 times as much as NADH in the solution. Each of $E_1$ and $E_2$ are used in the cycling reaction in an optional amount sufficient to carry out the cycling reaction. As this amount, an amount sufficient to attain a number of cycles which permits desired sensitization can be properly chosen depending on the amount of the component to be measured. For example, it is preferable to carry out 10 cycles or more of the reaction per minute. For this purpose, the amount of each enzyme used is preferably 1 to 100 units. When an electron carrier is used, its amount is preferably 0.01 to 10 mM. As the pH range for the cycling reaction, any pH range may be employed so long as in this range, the enzymes used are stable and act satisfactorily and the cycling reaction can be smoothly carried out. Usually, a pH range of approximately 6.0–9.5 may be employed by choosing a buffer solution properly. There can be used, for example, phosphate buffers and Good's buffers. The reaction is carried out usually at approximately 25°–40° C. for 1 minute or more, though the reaction temperature and the reaction time are not critical.

Next, for measuring a variable amount detectable in the cycling reaction, it is sufficient that the change of the amount of $S_1$ or $S_2$ consumed or the amount of $P_1$ or $P_2$ produced is measured. These components may be properly measured by a conventional method. Oxidase, peroxidase and the like which act on these components as a substrate, may be used singly or in combination. A particularly preferable example is as follows. When NADPH diaphorase is used as $E_1$ and a tetrazolium salt, 2,6-dichlorophenolindophenol or the like is used as $S_1$, the variable amount in the cycling reaction can be observed as color development or fading of a dye. Therefore, the variable amount in the cycling reaction can easily be measured colorimetrically by measuring absorbance with the lapse of time simultaneously with the reaction. It is also possible to measure the variable amount after terminating the cycling reaction. When NAD(P)H oxidase is used as $E_1$ and peroxidase is allowed to act in combination therewith to introduce $H_2O_2$ produced by NAD(P)H oxidase into a color-producing system, the variable amount in the cycling reaction can be measured either simultaneously with the reaction or after the termination of the reaction.

The amount of a component consumed in the cycling reaction or the amount of a component produced therein is thus determined, whereby the amount of NADH or ATP in the solution can be determined with high sensitivity by using a calibration curve for NADH or ATP, respectively. Furthermore, from the amount of NADH thus determined, one of factors in the enzymatic reaction system by dehydrogenase $E_0$ composed in the solution used, i.e., the enzymatic activity of $E_0$, the amount of $NAD^+$ and the amount of a substrate for dehydrogenase $E_0$, can be determined. From the amount of ATP determined, one of factors in the enzymatic reaction system by kinase composed in the solution used, i.e., the enzymatic activity of kinase, the amount of ADP and the amount of a phosphorus-containing compound as substrate for kinase, can be determined. When the NAD., the substrate A, the ADP or the phosphorus-containing compound as substrate for kinase is produced by another series of reactions, one of factors participating in a reaction carried out at the very first can be quantitatively determined after all.

The enzymes and necessary reagents which are used for carrying out the quantitation according to the present invention may be stored in the form of aqueous solution(s) or dry powder(s) as one system or a plurality of systems. The amounts of the enzymes and the necessary reagents used are determined and aqueous solutions of a proper combination of the enzymes and the reagents are used for the quantitation. Although the volumes of the aqueous solutions used per test are not critical, they are usually about 50 μl to about 5 ml. Although the volume of a solution to be subjected to the quantitation is also not critical, it is usually about 5 μl to about 5 ml.

The enzymatic reaction in the solution by which NADH is liberated and produced may be carried out either previously and separately, or simultaneously with the enzymatic reaction by NADH kinase in the same system. Then, the cycling reaction is carried out and a variable amount detectable in the reaction is measured.

EXAMPLES

The present invention is further illustrated with the following examples, which should not be construed as limiting the scope of the invention.

Example 1 (Preparation of NADH kinase)

*Pichia membranaefaciens* YS27 (FERM BP-3208) was inoculated into 50 ml of culture medium A (pH 5.5) consisting of 2% glucose, 1% yeast extract, 1% peptone, 0.9% monopotassium hydrogenphosphate, 0.6% ammonium sulfate, 0.05% calcium chloride and 0.05% magnesium sulfate in a 500-ml Sakaguchi flask, and was subjected to shaking culture at 30° C. for 24 hours. The seed culture thus obtained was inoculated into 20 liters of culture medium A and cultured at 30° C. for 18 hours in a 30-liters jar fermentor under conditions of an aeration rate of 20 liters/min and an agitation rate of 300 r.p.m. The resulting culture was collected by centrifugation to obtain 1,406 g of cells. The whole cells were inoculated into 20 liters of culture medium B (pH 5.5) consisting of 0.5% glucose, 1% yeast extract, 1% peptone, 0.9% monopotassium hydrogenphosphate, 0.6% ammonium sulfate, 0.05% calcium chloride, 0.05% magnesium sulfate and 2% sodium succinate, and cultured at 30° C. for 6 hours in a 30-liters jar fermentor under conditions of an aeration rate of 20 liters/min and an agitation rate of 300 r.p.m. The resulting culture was collected by centrifugation to obtain 1,428 g of cells. The whole cells were dispersed in 50 mM phosphate buffer (pH 6.0) containing 0.1M saccharose and 0.5% Triton X-100, to make a total volume of 5 liters, and the resulting dispersion was ground by the use of glass beads with a DYNO-MILL [WAB (Switzerland)].

Then, 5,280 ml of the liquid ground product recovered was freed of precipitate by centrifugation, and enzyme solution was dialyzed against 10 mM phosphate buffer (pH 6.0) containing 0.05M sodium chloride by using an ultrafiltration membrane (cut-off molecular weight: 6,000).

Subsequently, 5,260 ml of the enzyme solution thus obtained was passed through a CM-Sephadex C-50 column (Pharmacia AB) previously buffered with 10 mM phosphate buffer (pH 6.0) containing 0.05M sodium chloride, to be adsorbed thereon, and was washed with 10 mM phosphate buffer (pH 6.0) containing 0.1M sodium chloride. Thereafter, elution was carried out by means of a sodium chloride concentration gradient of 0.1 to 0.4M to collect an active fraction.

The buffer in 455 ml of the eluate was dialyzed against 10 mM HEPPS buffer (pH 7.5) containing 10% ammonium sulfate and 5 mM $MgCl_2$ by using an ultrafiltration membrane (cut-off molecular weight: 6,000). The solution thus obtained was passed through Phenyl-Toyopearl 650 column (Tosoh Ltd.) previously buffered with the same buffer as above, to be adsorbed thereon, and was washed with 10 mM HEPPS buffer (pH 7.5) containing 10% ammonium sulfate and 5 mM $MgCl_2$. Thereafter, elution was carried out by means of an ammonium sulfate concentration gradient of 10 to 0% to collect an active fraction.

Subsequently, 372 ml of the eluate was concentrated to a volume of 25 ml by the use of an ultrafiltration apparatus (cut-off molecular weight: 10,000) mfd. by Amicon, and charged into a Sephacryl S-300 HR column (mfd. by Pharmacia AB) previously buffered with 10 mM HEPPS buffer (pH 7.5) containing 0.2M ammonium sulfate and 5 mM $MgCl_2$, and gel filtration was carried out. The active fraction thus obtained was concentrated and then freeze-dried to obtain 117.3 mg (recovery: 34%) of a preparation of the present enzyme. The specific activity of this preparation was 102 U/mg.

Example 2 (Determination of NADH)

Figure 5:
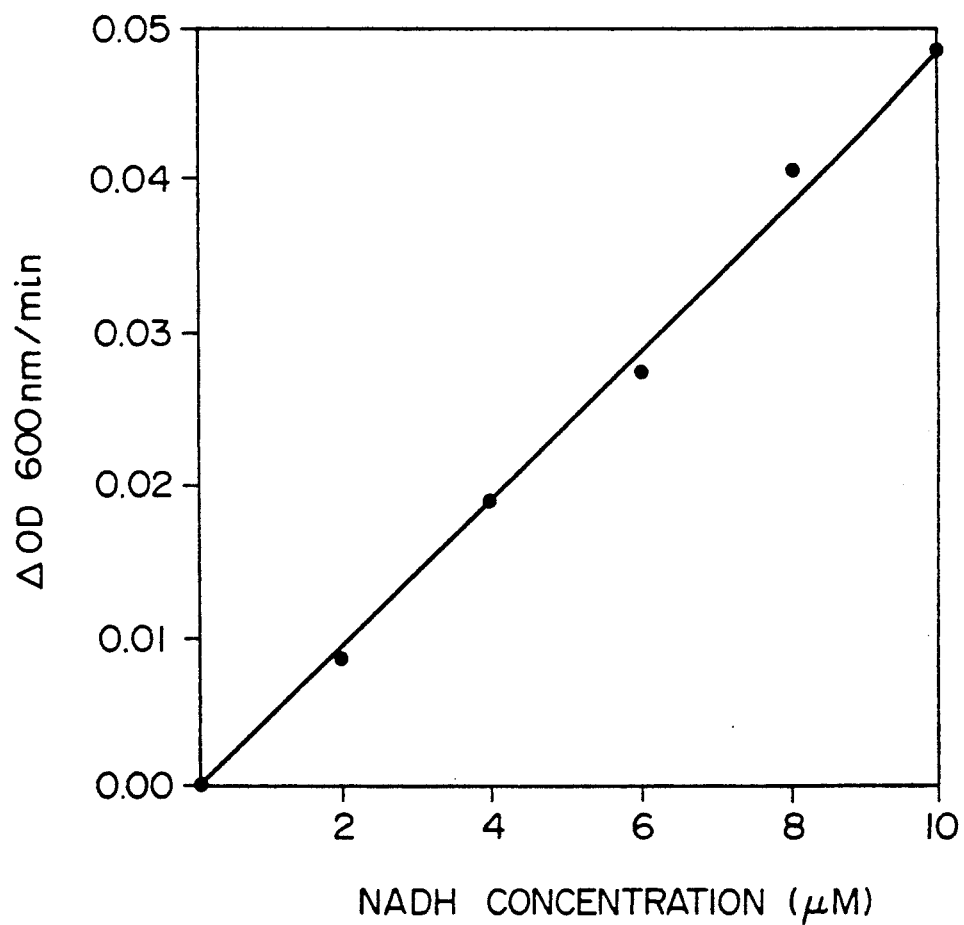
FIG. 5 shows a calibration curve obtained in Example 2 by plotting $\Delta OD_{600nm}$/min against NADH concentration.

For determining a slight amount of NADH present in a system containing a large amount of $NAD^+$, 0.4 ml of a sample solution containing 2 mM $NAD^+$ and each concentration (0 to 10 μM) of NADH was added to 0.8 ml of a reagent solution having the composition of reagent solution I shown below, and the reaction was carried out at 35° C. for 20 minutes. After terminating the reaction, 0.8 ml of a reagent solution having the composition of reagent solution II shown below was mixed with the reaction solution, and the resulting mixture was immediately introduced into a constant-temperature cuvette of STASAR III spectrophotometer of Gilford and subjected to reaction at 30° C. Simultaneously with this reaction, the change of absorbance at 600 nm was measured with the lapse of time, whereby the difference ($\Delta OD_{600nm}$/min) between absorbance values 1 minute and 2 minutes after the initiation of the coloration reaction was obtained as a measured value. Consequently, as shown in FIG. 5, good linearity could be attained between NADH concentration and $\Delta OD_{600nm}$/min with high sensitivity.

| Composition of reagent solution I (pH 8.5): | |
|---|---|
| 100 mM | HEPPS |
| 7.5 mM | ATP |
| 15 mM | magnesium chloride |
| 0.3 M | sodium acetate |
| 10 U/ml | NADH kinase (prepared in Example 1) |
| Composition of reagent solution II (pH 8.0): | |
| 10 mM | G-6-P |
| 50 mM | HEPPS |
| 10 mM | magnesium chloride |
| 0.1% | bovine serum albumin |
| 2.5 IU/ml | G-6-P dehydrogenase ($NADP^+$-dependent) |
| 5 IU/ml | diaphorase |
| 300 M | 2,6-dichlorophenolindophenol |

Example 3 (Determination of Sodium Cholate)

Figure 6:
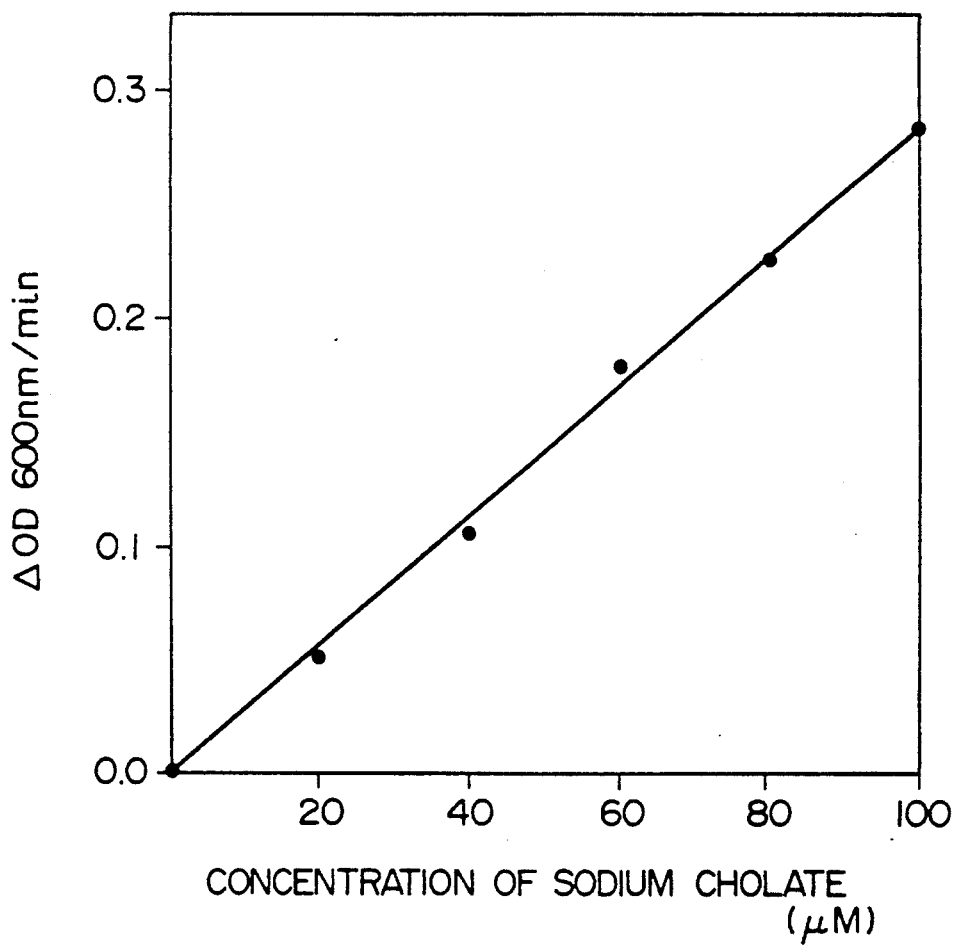
FIG. 6 shows a calibration curve obtained in Example 3 by plotting $\Delta OD_{600nm}$/min against sodium cholate concentration.

For determining a slight amount of sodium cholate, 80 μl of a sample solution containing each concentration (0 to 100 μM) of sodium cholate was added to 0.8 ml of a reagent solution having the composition of reagent solution I shown below, and the reaction was carried out at 35° C. for 20 minutes. After terminating the reaction, 0.8 ml of a reagent solution having the composition of reagent solution II shown below was mixed with the reaction solution, and the resulting mixture was immediately introduced into a constant-temperature cuvette of STASAR III spectrophotometer of Gilford and subjected to reaction at 30° C. Simultaneously with this reaction, the change of absorbance at 600 nm was measured with the lapse of time, whereby the difference ($\Delta OD_{600nm}$/min) between absorbance values 1 minute and 2 minutes after the initiation of the coloration reaction was determined as a measured value. Consequently, as shown in FIG. 6, good linearity could be attained between sodium cholate concentration and $\Delta OD_{600nm}$/min with high sensitivity.

| Composition of reagent solution I (pH 8.5): | |
|---|---|
| 67 mM | HEPPS |
| 5 mM | ATP |
| 10 mM | magnesium chloride |
| 0.2 M | sodium acetate |
| 2 mM | $NAD^+$ |
| 0.3 IU/ml | 3α-hydroxysteroid dehydrogenase |

| Composition of reagent solution I (pH 8.5): | |
|---|---|
| | (available from Oriental yeast Co., Ltd.) |
| 7 U/ml | NADH kinase (prepared in Example 1) |

Composition of reagent solution II

The same as the composition of reagent solution II used in Example 2.

Example 4 (Determination of Sodium Cholate)

Figure 7:
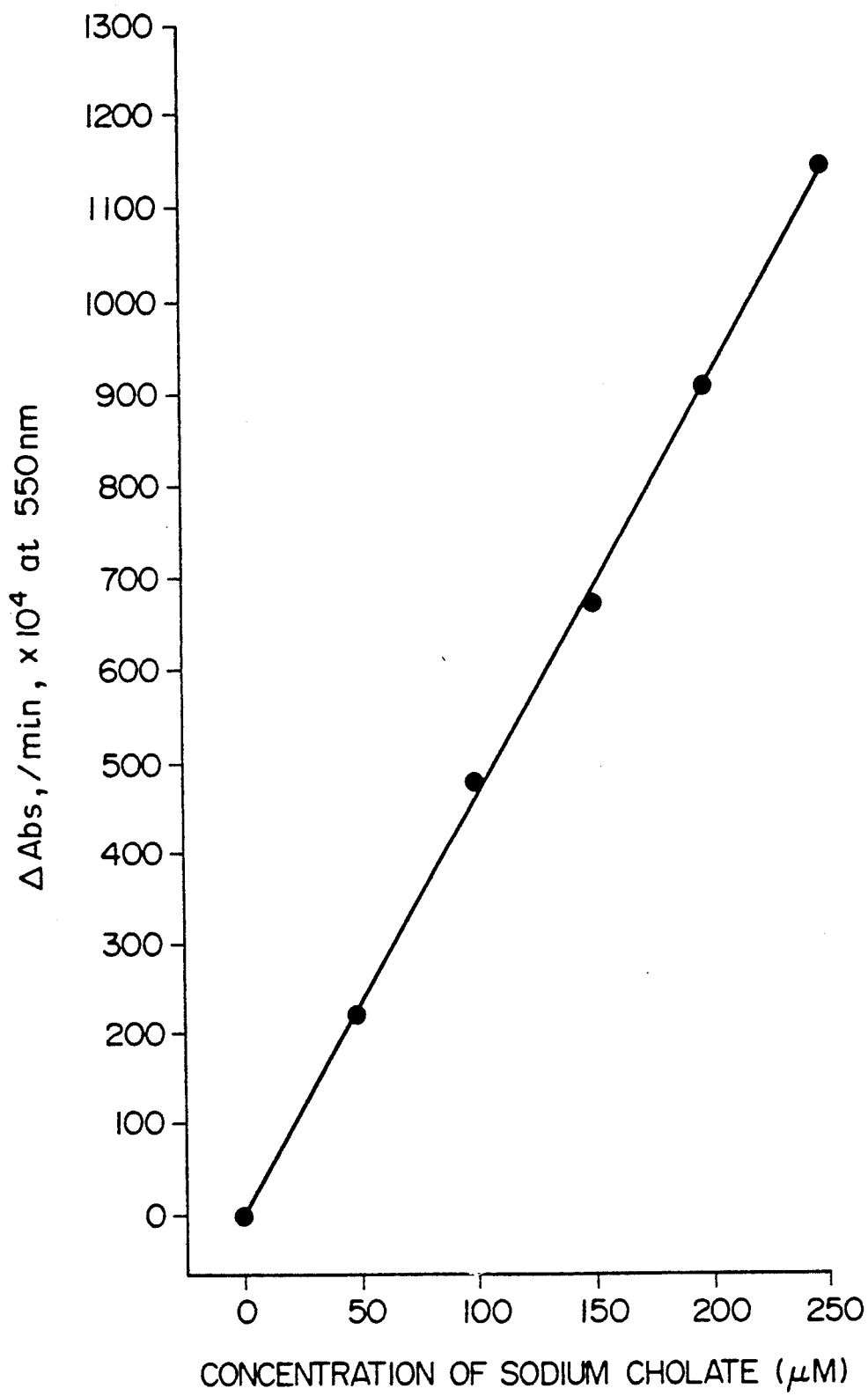
FIG. 7 shows a calibration curve obtained by the use of β-NAD+ in Example 4 by plotting $\Delta OD_{600nm}$/min against sodium cholate concentration.
Figure 8:
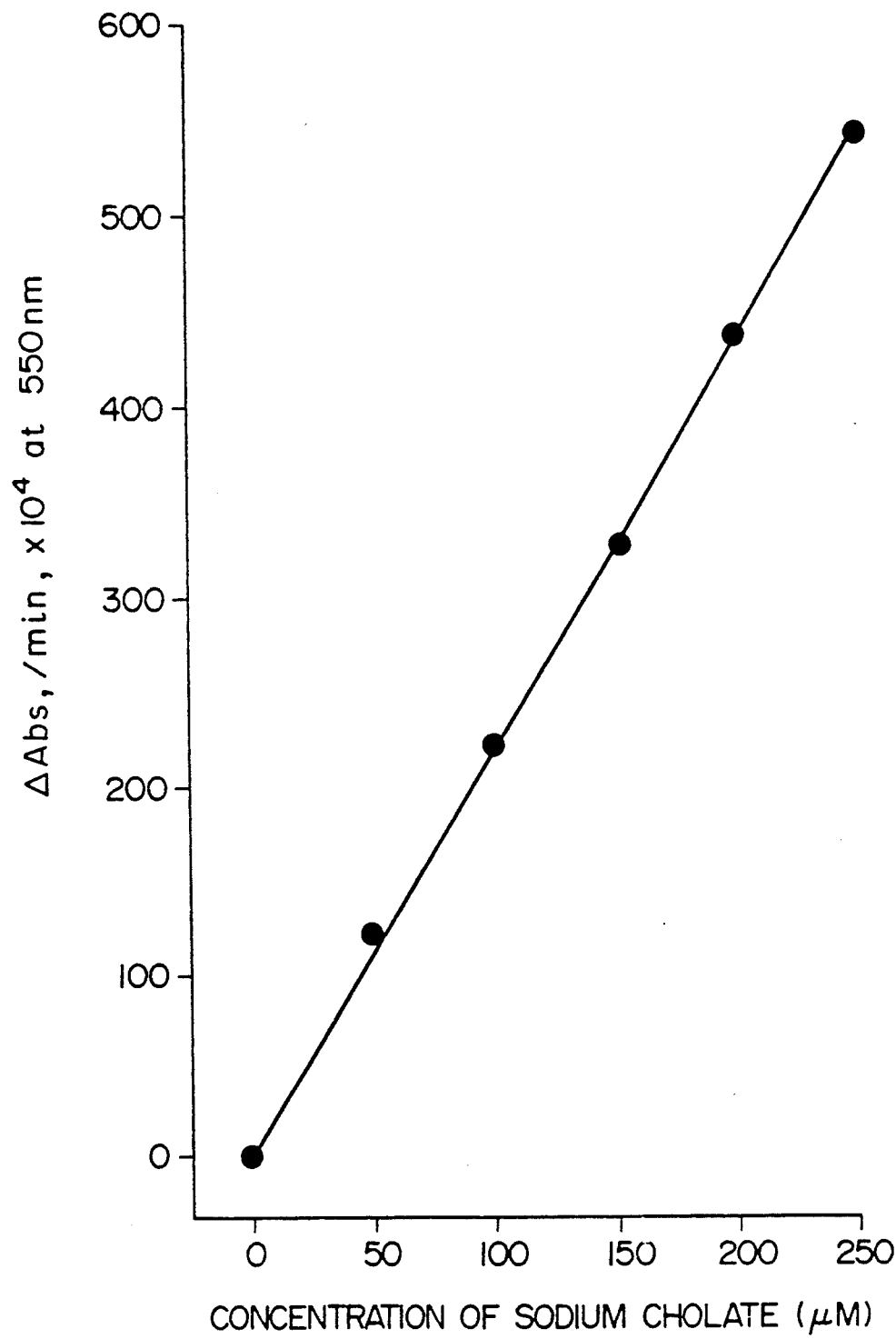
FIG. 8 shows a calibration curve obtained by the use of thio-NAD+ in Example 4 by plotting $\Delta OD_{550nm}$/min against sodium cholate concentration.

For determining a slight amount of sodium cholate, 50 μl of each of sodium cholate solutions having concentrations of 50, 100, 150, 200 and 250 μM, respectively, was added as a sample to 300 μl of a reagent solution having the composition of reagent solution I shown below. The resulting mixture was allowed to stand at 30° C. for 5 minutes, after which 300 μl of the NK solution shown below was added, and the reaction was carried out at 30° C. for 20 minutes. Then, 3.0 ml of a reagent solution having the composition of reagent solution II shown below was mixed with the reaction solution. The resulting mixture was subjected to reaction at 30° C., and the average change of absorbance at 550 nm per minute from 1 minutes after to 6 minutes after the initiation of the reaction was measured. Consequently, good linearity starting from the zero point could be attained with high sensitivity between sodium cholate concentration and average change of absorbance, up to a sodium cholate concentration of 200 μm, as shown in FIG. 7 in the case of using β-NAD+, and as shown in FIG. 8 in the case of using thio-NAD+.

| Composition of reagent solution I (pH 8.5): | |
|---|---|
| 65 mM | dipotassium phosphate |
| 8 mM | ATP |
| 20 mM | Magnesium chloride |
| 0.5 M | sodium acetate |
| 5 mM | NAD+ (β-form or thio-form) |
| 0.03% | bovine serum albumin |
| 10 IU/ml | 3α-hydroxysteroid dehydrogenase |
| Composition of NK solution: | |
| 7.7 U/ml | NADH kinase (prepared in Example 1) |
| 0.2 M | ammonium sulfate |
| Composition of reagent solution II (pH 8.0): | |
| 20 mM | G-6-P |
| 50 mM | dipotassium phosphate |
| 0.03% | bovine serum albumin |
| 1.2 mM | Nitrotetrazolium Blue |
| 0.1 M | EDTA-2Na |
| 0.5% | Triton X-100 |
| 3 IU/ml | G-6-P dehydrogenase derived from yeast (6 IU/ml in the case of thio-form) |
| 3 IU/ml | diaphorase derived from a bacillus (6 IU/ml of diaphorase derived from a clostridium, in the case of thio-form) |

Example 5 (Determination of Bile Acid in Serum)

Figure 9:
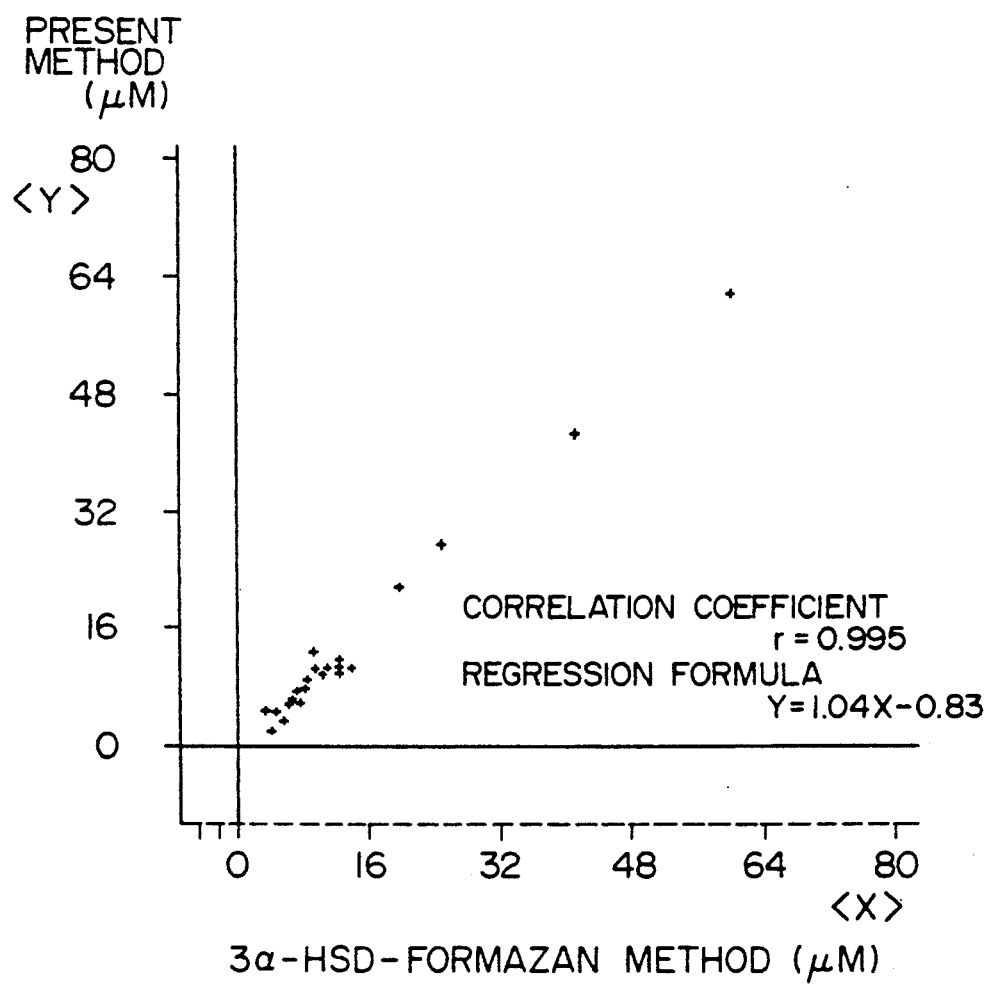
FIG. 9 is a diagram showing the correlation between measured values obtained by the present method and those obtained by the 3α-HSD-formazan method which was determined in Example 5.

For measuring the concentration of bile acid in serum, 200 μl of each of 24 human sera as samples or 200 μl of a 50 μM sodium cholate solution as standard solution was added to 300 μl of a reagent solution having the composition of reagent solution I shown below. The resulting mixture was allowed to stand at 30° C. for 5 minutes, after which 300 μl of the NK solution shown below was added, and the reaction was carried out at 30° C. for 20 minutes. Then, 3.0 ml of a reagent solution having the composition of reagent solution II was mixed with the reaction solution. The mixture thus obtained was subjected to reaction at 30° C., and the change of absorbance at 550 nm per minute from 2 minutes after to 3 minutes after the initiation of the reaction was measured. Measurement was carried out for the samples as above by a conventional method, the 3α-HSD-formazan method. Consequently, the comparison between the present method and 3α-HSD-formazan method was as shown in Table 4, and the correlation coefficient of 0.995 indicates good correlation between the two methods. The bile acid concentrations calculated on the basis of the change of absorbance in the standard solution were as shown in FIG. 9. From these results, it was found that the present method is in good correlation with the conventional method, i.e., the 3α-HSD-formazan method, and makes it possible to measure bile acid accurately with sensitivity higher than that of the 3α-HSD-formazan method.

| Composition of reagent solution I (pH 8.5): | |
|---|---|
| 65 mM | dipotassium phosphate |
| 12 mM | ATP |
| 20 mM | magnesium chloride |
| 0.75 M | sodium acetate |
| 7.5 mM | β-NAD+ |
| 0.03% | bovine serum albumin |
| 60 mM | potassium oxamate |
| 15 IU/ml | 3α-hydroxysteroid dehydrogenase |
| Composition of NK solution: | |
| 13.5 U/ml | NADH kinase (prepared in Example 1) |
| 0.2 M | ammonium sulfate |
| Composition of reagent solution II (pH 8.0): | |
| 20 mM | G-6-P |
| 50 m | dipotassium phosphate |
| 0.03% | bovine serum albumin |
| 1.2 mM | Nitrotetrazolium Blue |
| 0.1 m | EDTA-2Na |
| 0.5% | Triton X-100 |
| 3 IU/ml | G-6-P dehydrogenase derived from yeast |
| 3 IU/ml | diaphorase derived from a bacillus |
| 40 mM | potassium oxamate |

TABLE 4

| Sample | 3α-HSD-formazan method | Present method (NK method) |
|---|---|---|
| Standard solution | 471 | 1221 |
| Human serum 1 | 54 | 81 |
| Human serum 2 | 73 | 181 |
| Human serum 3 | 69 | 178 |
| Human serum 4 | 36 | 117 |
| Human serum 5 | 100 | 239 |
| Human serum 6 | 63 | 159 |
| Human serum 7 | 90 | 249 |
| Human serum 8 | 70 | 190 |
| Human serum 9 | 73 | 149 |
| Human serum 10 | 44 | 115 |
| Human serum 11 | 104 | 256 |
| Human | 80 | 220 |

TABLE 4-continued

| Sample | 3α-HSD-formazan method | Present method (NK method) |
|---|---|---|
| Human serum 12 | 59 | 139 |
| Human serum 13 | 120 | 337 |
| Human serum 14 | 89 | 313 |
| Human serum 15 | 118 | 239 |
| Human serum 16 | 133 | 256 |
| Human serum 17 | 120 | 264 |
| Human serum 18 | 41 | 85 |
| Human serum 19 | 79 | 190 |
| Human serum 20 | 384 | 1033 |
| Human serum 21 | 236 | 664 |
| Human serum 22 | 565 | 1490 |
| Human serum 23 | 188 | 518 |
| Human serum 24 | | |

Formazan method: Absorbance × $10^4$ at 550 nm
present method: Absorbance × $10^4$ at 550 nm

Example 6 (Determination of 3-Hydroxybutyrate Dehydrogenase)

Figure 10:
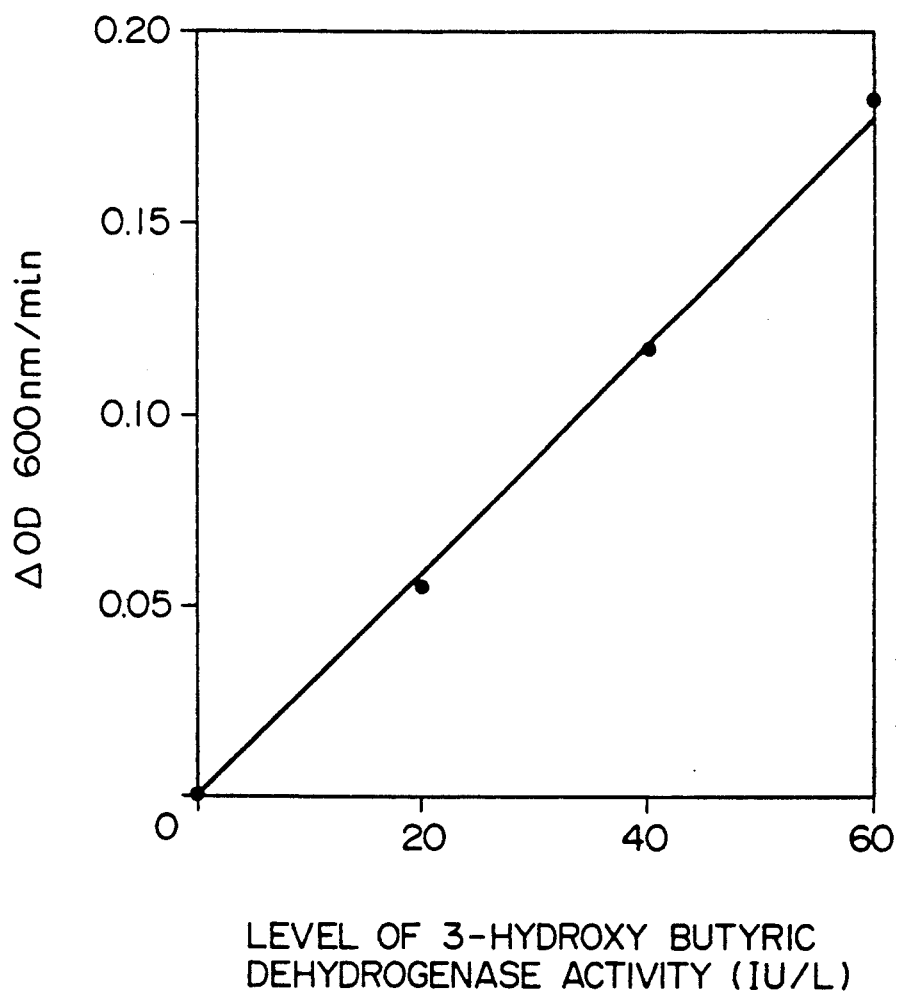
FIG. 10 is a calibration curve obtained in Example 6 by plotting $\Delta OD_{600nm}$/min against the level of 3-hydroxybutylate dehydrogenase activity.

For determining a slight amount of 3-hydroxybutyrate dehydrogenase, 400 μl of a sample solution containing each concentration (0 to 60 IU/liter) of 3-hydroxybutyrate dehydrogenase was added to 0.8 ml of a reagent solution having the composition of reagent solution I shown below, and the reaction was carried out at 35° C. for 10 minutes. After terminating the reaction, 0.8 ml of a reagent solution having the composition of reagent solution II shown below was mixed with the reaction solution, and the resulting mixture was immediately introduced into a constant-temperature cuvette of a spectrophotometer and subjected to reaction at 30° C. Simultaneously with this reaction, the change of absorbance at 600 nm was measured with the lapse of time, whereby the difference ($\Delta OD_{600nm}$/min) between absorbance values 1 minute and 2 minutes after the initiation of the coloration reaction was obtained as a measured value. Consequently, as shown in FIG. 10, good linearity could be attained between the level of 3-hydroxybutyrate activity and $\Delta OD_{600nm}$/min with high sensitivity.

| Composition of reagent solution I (pH 8.5): | |
|---|---|
| 100 mM | HEPPS |
| 7.5 Mm | ATP |
| 15 Mm | magnesium chloride |
| 0.3 M | sodium acetate |
| 3 mM | β-NAD+ |
| 90 mM | 3-hydroxybutyric acid |
| 10 U/ml | NADH kinase (prepared in Example 1) |

Composition of Reagent Solution II

The same as the composition of reagent solution II used in Example 2.

Example 7 (Determination of Glycerin)

Figure 11:
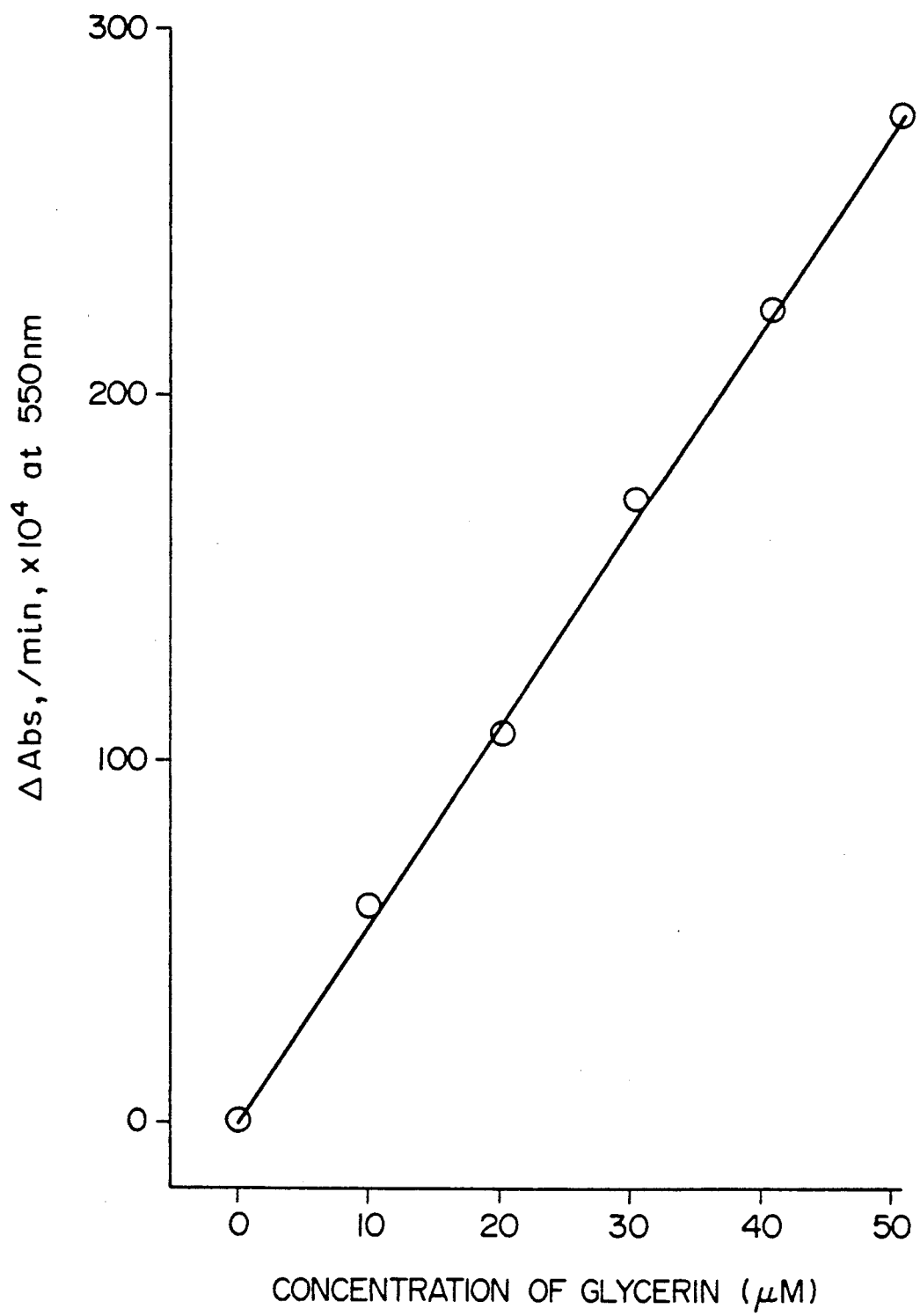
FIG. 11 is a calibration curve obtained in Example 7 by plotting $\Delta OD_{550nm}$/min against glycerin concentration.

For determining a slight amount of glycerin, 50 μl of each of glycerin solutions having concentrations of 10, 20, 30, 40 and 50 μM, respectively, was added as a sample to 300 μl of a reagent solution having the composition of reagent solution I shown below. The resulting mixture was allowed to stand at 30° C. for 5 minutes, after which 300 μl of the NK solution shown below was added, and the reaction was carried out at 30° C. for 20 minutes. Then, 3.0 ml of a reagent solution having the composition of reagent solution II shown below was mixed with the reaction solution. The mixture thus obtained was subjected to reaction at 30° C., and the change of absorbance at 550 nm per minute from 1 minute after to 6 minutes after the initiation of the reaction. Consequently, as shown in FIG. 11, good linearity starting from the zero point was attained between glycerin concentration and the average change of absorbance with high sensitivity.

| Composition of reagent solution I (pH 9.0): | |
|---|---|
| 65 mM | tris(hydroxymethyl)aminomethane |
| 8 mM | ATP |
| 20 mM | magnesium chloride |
| 0.5 M | sodium acetate |
| 5 mM | β-NAD+ |
| 0.03% | bovine serum albumin |
| 7 IU/ml | glycerol dehydrogenase |
| Composition of NK solution: | |
| 7.7 U/ml | NADH kinase (prepared in Example 1) |
| 0.2 M | ammonium sulfate |
| Composition of reagent solution II (pH 8.0): | |
| 50 mM | dipotassium phosphate |
| .03% | bovine serum albumin |
| 1.2 mM | Nitrotetrazolium Blue |
| 0.1 M | EDTA-2Na |
| 0.5% | Triton X-100 |
| 3 IU/ml | G-6-P dehydrogenase derived from yeast |
| 3 IU/ml | diaphorase derived from a bacillus |

Example 8 (Determination of Alcohol Dehydrogenase)

Figure 12:
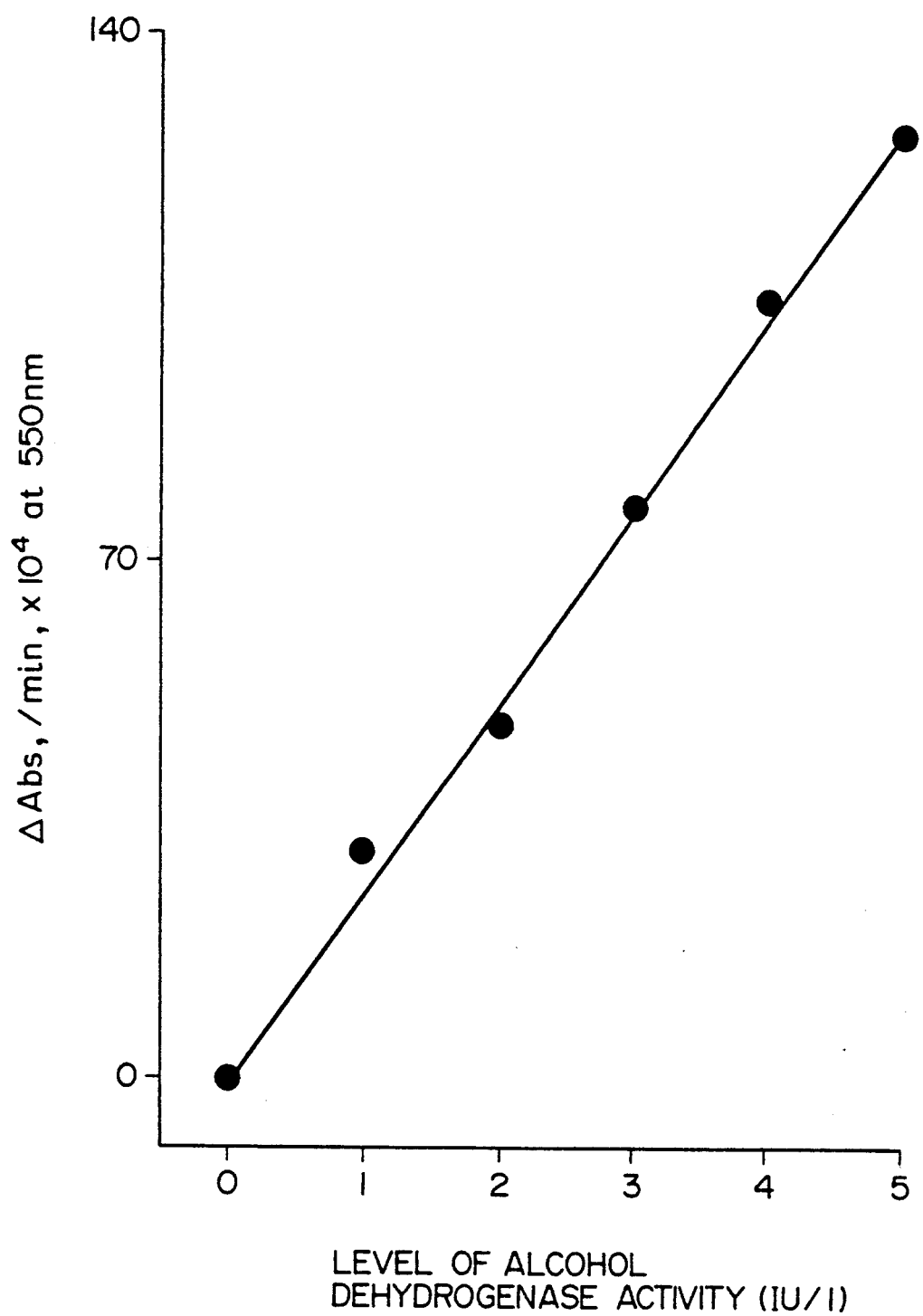
FIG. 12 is a calibration curve obtained in Example 8 by plotting $\Delta OD_{550nm}$/min against the level of alcohol dehydrogenase activity.

For determining a slight amount of alcohol dehydrogenase, 50 μl of each of alcohol dehydrogenase solutions having enzyme concentrations of 1, 2, 3, 4 and 5 IU/liter), respectively, was added as a sample to 300 μl of a reagent solution having the composition of reagent solution I shown below. The resulting mixture was allowed to stand at 30° C. for 10 minutes, after which 300 μl of the NK solution shown below was added, and the reaction was carried out at 30° C. for 20 minutes. Then, 3.0 ml of a reagent solution having the composition of reagent solution II shown below was mixed with the reaction solution. The mixture was obtained was subjected to reaction at 30° C., and the average change of absorbance at 550 nm per minute from 1 minute after to 6 minutes after the initiation of the reaction was measured. Consequently, as shown in FIG. 12, good linearity starting from the zero point could be attained between the level of alcohol dehydrogenase activity and the average change of absorbance with high sensitivity.

| Composition of reagent I (pH 9.0): | |
|---|---|
| 65 mM | glycylglycine |
| 8 mM | ATP |
| 20 mM | magnesium chloride |
| 0.5 M | sodium acetate |

| | -continued |
|---|---|
| 0.4 mM | thio-NAD+ |
| 0.03% | bovine serum albumin |
| 50 mM | n-amyl alcohol |
| Composition of NK solution: | |
| 7.7 U/ml | NADH kinase (prepared in Example 1) |
| 0.2 M | ammonium sulfate |
| Composition of reagent solution II (pH 8.0): | |
| 20 mM | G-6-P |
| 50 mM | dipotassium phosphate |
| 0.03% | bovine serum albumin |
| 1.2 mM | Nitrotetrazolium Blue |
| 0.1 M | EDTA-2Na |
| 0.5% | Triton X-100 |
| 6 IU/ml | G-6-P dehydrogenase derived from yeast |
| 6 IU/ml | diaphorase derived from a clostridium |

Example 9 (Determination of ATP)

Figure 13:
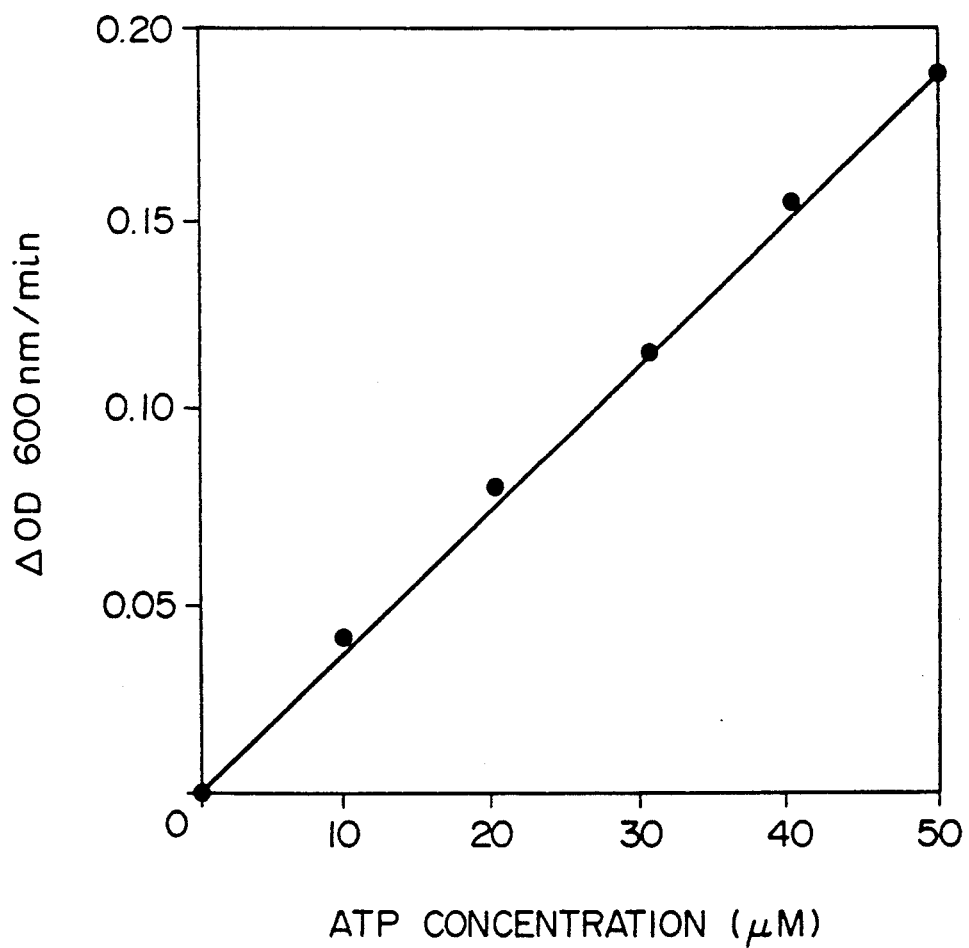
FIG. 13 is a calibration curve obtained in Example 9 by plotting $\Delta OD_{600nm}$/min against ATP concentration.

For determining a slight amount of ATP, 400 μl of a sample solution containing each concentration (0 to 50 μM) of ATP was added to 0.8 ml of a reagent solution having the composition of reagent solution I shown below, and the reaction was carried out at 35° C. for 20 minutes. After terminating the reaction, 0.8 ml of a reagent solution having the composition of reagent solution II shown below was mixed with the reaction solution, and the resulting mixture was immediately introduced into a constant-temperature cuvette of a spectrophotometer and subjected to reaction at 30° C. Simultaneously with this reaction, the change of absorbance at 600 nm was measured with the lapse of time, whereby the difference ($\Delta OD_{600nm}$/min) between absorbance values 1 minute and 2 minutes after the initiation of the coloration reaction was determined as a measured value. Consequently, as shown in FIG. 13, good linearity could be attained between ATP concentration and $\Delta OD_{600nm}$/min with high sensitivity.

| Composition of reagent solution I (pH 8.5): | |
|---|---|
| 100 mM | HEPPS |
| 3 mM | NADH |
| 15 mM | magnesium chloride |
| 0.3 M | sodium acetate |
| 10 U/ml | NADH kinase (prepared in Example 1) |

Composition of Reagent Solution II

The same as the composition of reagent solution II used in Example 2.

The determination method of the present invention is a novel method which permits highly sensitive determination of a slight amount of NADH in a system containing NAD+ and NADH as a mixture, without any influence of NAD+. Furthermore, the method permits satisfactory measurement of one of the following components: enzyme activities participating in various enzymatic reaction systems using NAD+ or ADP as a substrate, NAD+, ADP, and substrates which react together therewith. Accordingly, the method makes it possible to determine the amount of a substance capable of serving as a marker of pathosis, accurately with high sensitivity in a short time in diagnoses of diseases and the like, and it is applicable to automatic analysis, so that an exact diagnosis can be made. Therefore, the method is industrially very useful in the fields of clinical medicine, etc.

We claim:

1. A method of highly sensitive determination of NADH which comprises allowing an NADH kinase highly specific for NADH, prepared by culturing *Pichia membranaefaciens* YS27 (FERM BP-3208), to act on a solution containing NAD+ and NADH in the presence of (i) at least one divalent metal ion selected from the group consisting of $Mg^{2+}$, $Mn^{2+}$, $Ca^{2+}$ and $Co^{2+}$ and (ii) XTP wherein X is adenosine, uridine, guanosine, cytidine, inosine, thymidine, deoxyadenosine, deoxyuridine, deoxyguanosine, deoxycytidine or deoxyinosine to produce NADPH and XDP wherein X is defined as above, subjecting the NADPH to a cycling reaction using catalytic reactions capable of oxidizing NADPH into NADP+ and reducing NADP+ into NADPH, measuring the variable amount of a substrate consumed or a product produced by the cycling reaction to determine the amount of only the NADH in the mixed solution containing NAD+ and NADH.

2. A method according to claim 1, wherein NAD+ is β-NAD+, thio-NAD+ or α-NAD+, and NADH is β-NADH, thio-NADH or α-NADH.

* * * * *